United States Patent [19]

Della Badia et al.

[11] Patent Number: 5,397,325
[45] Date of Patent: Mar. 14, 1995

[54] LAPAROSCOPIC SUTURING DEVICE

[75] Inventors: Carl Della Badia, Voorhes; Carl J. Costello, Runnemede, both of N.J.

[73] Assignee: Badiaco, Inc., Voorhees, N.J.

[21] Appl. No.: 149,234

[22] Filed: Nov. 9, 1993

[51] Int. Cl.$^6$ .............................................. A61B 17/00
[52] U.S. Cl. ..................... 606/144; 606/148; 606/207; 112/80.03; 112/169
[58] Field of Search ..................... 606/1, 139, 144–148, 606/151, 205, 207, 211; 112/80.03, 169

[56] References Cited

U.S. PATENT DOCUMENTS

| | | | |
|---|---|---|---|
| 1,933,024 | 10/1933 | Nagelmann | 606/145 |
| 3,090,386 | 5/1963 | Curtis | 606/146 |
| 3,946,740 | 3/1976 | Bassett | 606/145 |
| 4,923,461 | 5/1990 | Caspari et al. | 606/148 |
| 5,147,373 | 9/1992 | Ferzli | 606/148 |
| 5,275,613 | 1/1994 | Haber et al. | 606/148 |
| 5,281,220 | 1/1994 | Blake, III | 606/205 |
| 5,318,577 | 6/1994 | Li | 606/147 |

FOREIGN PATENT DOCUMENTS

535906 4/1993 European Pat. Off. ............ 606/148

Primary Examiner—Stephen C. Pellegrino
Assistant Examiner—Jeffrey A. Schmidt
Attorney, Agent, or Firm—Peter A. Borsari

[57] ABSTRACT

The present invention relates to surgical suturing devices, particularly for use in laparoscopic surgery. The surgical suturing device has a tubular elongated shaft terminating into a jaw assembly at the distal end and a handle assembly at the proximal end thereof. The jaw assembly includes a first jaw member pivotally connected to a second jaw member. An actuator rod extending longitudinally within the length of said shaft is connected at its proximal end to said handle assembly and is pivotally connected at its distal end to said jaw assembly. The underside of said first jaw member is provided with a cupped recess having a wheel assembly disposed therein. The wheel assembly includes a needle mount for securably retaining a needle and is configured such that the needle lies within the cupped recess when the jaw members are closed and can be deployed in a protracted position away from the first jaw member when the jaw members are in an open position. In operation, the suturing device offers superior control over both the needle and the tissue to be sutured.

14 Claims, 4 Drawing Sheets

LAPAROSCOPIC SUTURING DEVICE

FIELD OF INVENTION

The present invention relates to a surgical suturing instrument, particularly for use, for example, in non-open surgery, and more particularly for use, for example, in laparoscopic surgery. More specifically, the present invention provides a suturing device comprising a jaw assembly having first and second jaw members, wherein said first jaw member is provided with a cupped recess having means for securably retaining a needle such that the needle lies within the cupped recess when the jaw members are in a closed position and can be extended away from the first jaw member when the jaw members are in an open position. The jaw assembly also is utilized to grasp and stabilize tissue between the opposed jaw members. In this manner, the suturing device functions both as a needle holder and as a clamping device. In operation and use, the suturing device offers superior control over both the needle and the tissue being sutured.

BACKGROUND OF THE INVENTION

The prior art is replete with surgical suturing devices, including surgical needle holders, devices which force a surgical needle through tissue and instruments which grasp and stabilize tissue to be sutured between opposed jaws. Surgical instruments also are known in the art which provide adequate control over both the suturing needle and the tissue to be sutured. For instance, in the field of open surgery, surgical tools which both grasp thick tissue and force the needle therethrough are known, as represented by U.S. Pat. No. 2,213,830 to Anastasi and U.S. Pat. No. 1,933,024 to Nagelmann. These devices comprise scissor-like arms which expand laterally when opened. Although appropriate for use in open surgery, such devices are unsuitable for use in non-open surgery since they cannot be introduced through a tubular conduit and their bulky design cannot be modified to conform with the restricted operating space associated with non-open surgery.

Non-open surgeries, such as arthroscopic surgery and laparoscopic surgery, recently have become widely practiced surgical procedures. Such procedures have gained rapid popularity and generally are preferable over the traditional open surgery which requires cutting large incisions through the skin, muscles and membranes to open and expose the body cavity, thereby necessitating longer hospitalization stays and prolonged recovery periods. In non-open surgery, small incisions are made into which tubular conduits, such as cannulae and trocars, are inserted and directed to the site of the operable internal organ or tissue. One or more surgical instruments are introduced through the tubular conduits in order to perform the surgical procedure.

Two fields of non-open surgery are commonly practiced today: shallow surgery, such as arthroscopic surgery, and deep surgery, such as laparoscopic surgery. The arthroscopic procedure typically is performed on body parts located near the skin surface, such as the knee or elbow, for repairing tears of the cartilage or meniscus, shaving irregular, roughened patella and other surfaces, and the like. In arthroscopic surgery, one or more small openings are made in the skin layer as to provide access for an elongated sleeve which is inserted through the surgical opening for receiving surgical instruments.

The laparoscopic procedure generally involves creating small incisions through the navel and through the abdominal wall for viewing and operating on internal areas of the body, such as the uterus, ovaries, gall bladder and appendix. Typically, a trocar tube is introduced through the navel incision for receiving a camera, magnifying lens or other fiber optic device for viewing the surgery. One or more additional trocar tubes are introduced through incisions in the abdominal wall such that laparoscopic surgical tools can be inserted through the tube(s) for manipulating, cutting and/or suturing an internal organ or tissue. In this manner, while viewing a video monitor via the fiber optic device positioned in the navel trocar, the surgeon can grasp an organ or tissue with one surgical tool and simultaneously cut or suture with another surgical device.

The evolution of non-open surgery has given rise to the need of single-shaft surgical instruments which can be inserted through a trocar and easily manipulated by a surgeon. These instruments are fashioned such that they can be inserted lengthwise through the trocar and comprise hand-held controls on the proximal end thereof to operate the distal, tissue-manipulating end of said instrument. Single shaft devices must have a sufficiently small diameter so that they can be inserted into a trocar tube and guided to the operative tissue site. Typically, such instruments are designed to perform one function, such as grasping and stabilizing tissue, cutting tissue, holding a suturing needle or pulling a suturing needle through tissue. A major drawback to non-open surgery is that it requires exceptional motor coordination to grasp and stabilize an organ or tissue with one surgical tool and performing a cutting or suturing procedure on said organ or tissue with a second surgical device, all while viewing a two dimensional video monitor. This disadvantage is particularly acute in performing a laparoscopic suturing procedure.

In laparoscopic suturing, thick tissue, such as uterine tissue, is oftentimes encountered. Consequently, the suturing needle must be of a length sufficient to pass through the tissue being sutured. Typically, the length of these needles is greater than the diameter of the single shaft suturing instruments. As a result, the suturing needle must be inserted lengthwise through a trocar. In the conventional laparoscopic suturing procedure typically practiced today, a straight Semm needle holder having opposing jaws at one end is used in the suturing procedure. This type of needle holder essentially is a clamping device which holds the suturing needle lengthwise between opposing jaws such that it can be introduced through a trocar and guided to the incision site. The tissue to be sutured is grasped by a clamping device which has been previously introduced through a second trocar to the incision site. The suturing needle is repositioned so that the needle is held transversely between the opposed jaws of the conventional needle holder and thereafter is pushed into the first layer of tissue. Oftentimes, the needle does not pass completely through the first layer of tissue and difficulty is encountered in finding the needle in the tissue mass. Once the needle is located, the needle has to be regrasped by the conventional needle holder and pulled through the layer of tissue. The needle again is released, repositioned and regrasped by the needle holder such that it is ready to be passed through the second layer of tissue. An additional problem often encountered with the use of the conventional needle holder is that the needle can slip out of the needle holder if it is not grasped properly or if the tissue is thick.

Accordingly, prior art needle holders for use in laparoscopic surgery have provided the surgeon with inadequate control over both the needle and the tissue to be sutured. The conventional clamping-type devices, described above and in use today, require the needle to be positively grasped between opposed jaws, which can result in slipping, mispositioning, or even premature release of the needle from the jaws during suturing manipulations. Consequently, because of the difficulties encountered in learning and practicing laparoscopic suturing techniques, many surgeons practicing laparoscopic surgery have opted to use single shaft stapling devices as a substitute for conventional suturing. These stapling devices are very expensive to use and significantly increase the cost of laparoscopic surgery.

Other single shaft devices are in use today specifically fashioned for holding a needle, thereby providing adequate needle control. However, since these instruments do not offer means to grasp and stabilize the tissue, which is slippery by nature, the tissue tends to evade needle carrier manipulation or must be grasped by a second instrument. As a result, the surgeon encounters difficulty in controlling and positioning both the needle and the tissue simultaneously, and the patient can suffer complications such as frayed tissue, errant punctures, inadequate stitches, extended surgical duration, hemorrhaging, and the like.

U.S. Pat. No. 4,493,323 to Albright et al. and U.S. Pat. No. 4,621,640 to Mulhollan et al. are representative of prior art suturing instruments for internal suturing without requiring open surgery and are particularly designed for use in arthroscopic surgery, specifically knee surgery. However, such suturing devices require the needle to be continuously manipulated as it progresses through the tissue layer being sutured. Albright et al. provides a device comprising a pair of needles which are forced outwardly through the end of an elongated tube by a plunger in order to penetrate and extend through the tissue to be sutured, the pair of needles then are forced outwardly through the skin layer of the patient so that they can be grasped by the surgeon, and are pulled to position a suture thread loop attached to the needles. For obvious reasons, such a device cannot be used in laparoscopic surgery. Mulhollan et al. discloses a mechanical needle carrier for carrying, gripping and manipulating a suturing needle within the body, particularly a knee joint. The Mulhollan device is inserted through a cannula or tube wherein the needle is guided to the knee tissue. The needle carrying device is positioned such that the needle end can puncture the tissue and the needle thereafter is released from the carrying device. The entire instrument must be withdrawn from the cannula in order to allow insertion of another instrument which pulls the needle through the conduit so that the suture can be tied and set. Although Mulhollan renders better manipulative control over the surgical needle, it is incapable of providing control over the tissue in concert with the needle.

Other suturing devices are known in the arthroscopic surgical art which address the problems of needle control and tissue control by permanently mounting a needle on one of two opposed jaws, thus eliminating the surgeons need to positively grasp and hold the needle by clamping means. These instruments are designed such that the opposed jaws grasp the tissue to be sutured, thereby providing positioning and control of the tissue as the needle punctures the tissue. Such a device is exemplified by U.S. Pat. No. 4,957,498 to Caspari et al. Caspari discloses a suturing instrument for use in arthroscopic surgery comprising a tubular shaft having a jaw assembly at the distal end thereof. A short, curved, hollow needle is affixed to the lower jaw. A suturing thread, originating from a spool mechanism positioned at the proximal end of the tubular shaft, is passed through said shaft and extends longitudinally through the hollow needle. In operation, the instrument drives the needle through the tissue to be sutured while clamping the tissue between the upper and lower jaws. However, the Caspari device does not provide a means of releasing the needle from the needle-holding device after its passage through the tissue. As a result, the surgeon is restricted to a double-pass type of stitch: upon closing of the jaws and the resultant tissue puncture, the suture is passed through the hollow needle, hooked by the jaw opposing the needle-holding jaw, and then pulled back through the hole made by its first pass through the tissue.

Related disadvantages with the Caspari device include the fact the needle is integral with the needle holding device and must be a hollow needle. Moreover, the Caspari needle holder more easily lends itself to breakage due to its intricate design and many parts. Further, the device more readily can become clogged with blood and debris, thereby rendering it ineffective, and is difficult to clean and maintain. Additionally, the Caspari instrument is not suitable for and cannot be adapted for use in a laparoscopic procedure where thick layers of tissue require suturing for several reasons. First, the permanently affixed hollow needle is of insufficient length and as such cannot pass through the thick tissue encountered in laparoscopic surgery. Second, the design of the Caspari device would not allow substitution of a longer suturing needle suitable for laparoscopic surgery because such a needle would prevent the jaw assembly from closing, thereby prohibiting the introduction of the instrument into a laparoscopic trocar.

There still exists a need for a suturing instrument, capable of being introduced through a cannula, trocar or similar conduit to the incision site, which provides superior control over both the suturing needle and the tissue to be sutured. Such a device should provide means whereby a surgeon is afforded with the flexibility of choosing different types of surgical needles, rather than restricting the surgeon to a specific, built-in needle. The device should further provide means for grasping, stabilizing and controlling the tissue being sutured. Additionally, the suturing device should be capable of securably retaining a surgical device whereby the surgeon is not required to positively grasp the needle (thereby risking loss of needle control) and the device also should be capable of releasing the surgical needle once the needle has pierced the tissue layer. Finally, the suturing device should be of a design which is easy to use, inexpensive to manufacture and lends itself to easy cleaning and maintenance.

SUMMARY OF THE INVENTION

Accordingly, it is an object of the present invention to provide a suturing device which offers superior control of the suturing needle while the tissue is being sutured.

It is another object of the present invention to provide a suturing device which can be introduced through, for example, a laparoscopic trocar, a cannula or like conduit.

It is yet another object of the present invention to provide a suturing device which enables the surgeon to control the manipulation of both the needle and the tissue to be sutured using one instrument.

It is a further object of the present invention to provide a suturing device which eliminates the need for grasping and stabilizing the tissue during the insertion of a needle.

It is an additional object of the present invention to provide a suturing device which provides greater control to the surgeon, thereby making suturing available in situations where it generally is not considered suitable.

It is still a further object of the present invention to provide a suturing device which is easy to use and easy to teach the use thereof, thereby lessening the complications associated with laparoscopic surgery.

It is another object of the present invention to provide a suturing device which is easy to use and can replace the use of expensive stapling devices, thereby saving on the cost of surgery.

It is yet an additional object of the present invention to provide a suturing device comprising a structure with fewer pans, thereby lessening the costs of manufacture.

It is another object of the present invention to provide a suturing device which is easy to clean and maintain.

It is a further object of the present invention to provide a needle holder which accommodates various types of standard surgical needles, thereby offering a surgeon flexibility in the choice of suturing needles.

It is another object of the present invention to provide a needle holder which allows for the use of various size and curvature of needles.

It is still another object of the present invention to provide a suturing device which provides a means for securably retaining a suturing needle and for releasing the needle after the needle punctures and passes through the tissue.

It is yet another object of the present invention to provide a suturing device which allows for reattachment of the needle to the suturing device after the needle has been released from said device, in order to initiate an additional suturing procedure.

It is an additional object of the present invention to provide a suturing device which provides a single use instrument having disposable heads.

These and other objects of the invention, as embodied and broadly described herein, are achieved by providing the present suturing device, useful, for example, in operations deep within body cavities without requiring open surgery, and is more particularly useful, for example, in laparoscopic surgery. The suturing device of the present invention comprises a tubular elongated shaft having a handle assembly at the proximal end, thereby providing control of said device, and a jaw element at the distal end, said jaw element being fashioned to releasably mount a suturing needle. The jaw element at the distal end of the device not only provides means to retain the needle but also functions as a clamping member for grasping and stabilizing the tissue to be sutured. In this manner, the device offers superior positioning means of the suturing needle relative to the tissue being sutured. In an alternative embodiment, the device may be in the form of a single use instrument with the jaw element being incorporated in a disposable head.

In operation, the use of the suturing device of the present invention offers a surgeon superior control over both the needle and the tissue to be sutured and the choice of various standard surgical needles. The device enables the surgeon to introduce the device through a laparoscopic trocar, cannula or similar conduit by providing means whereby the suturing needle lies within a cupped recess in the upper jaw when the opposed jaws are closed. Once the distal end of the device has been guided to the incision site, the jaws are opened and suturing needle is deployed from the cupped recess into a protracted, suturing position. In use, the open jaw members grasp and stabilize the tissue to be sutured, the needle punctures and passes through the tissue and is then released from suturing device for further suturing manipulations.

Additional objects, advantages and novel features of the invention will be set forth in part in the description which follows, and in part will become apparent to those skilled in the art upon examination of the following specification or may be learned by practice of this invention.

BRIEF DESCRIPTION OF THE DRAWINGS

The present invention will be better understood with reference to the appended drawing sheets, wherein.

DETAILED DESCRIPTION

The present invention relates to surgical suturing devices, particularly for use, for example, in operations deep within body cavities without requiring open surgery, and more particularly for use, for example, in laparoscopic surgery. The suturing device provides a needle holder which offers a surgeon superior manipulative control over both the needle and the tissue to be sutured.

Figures 1, 2, 3:
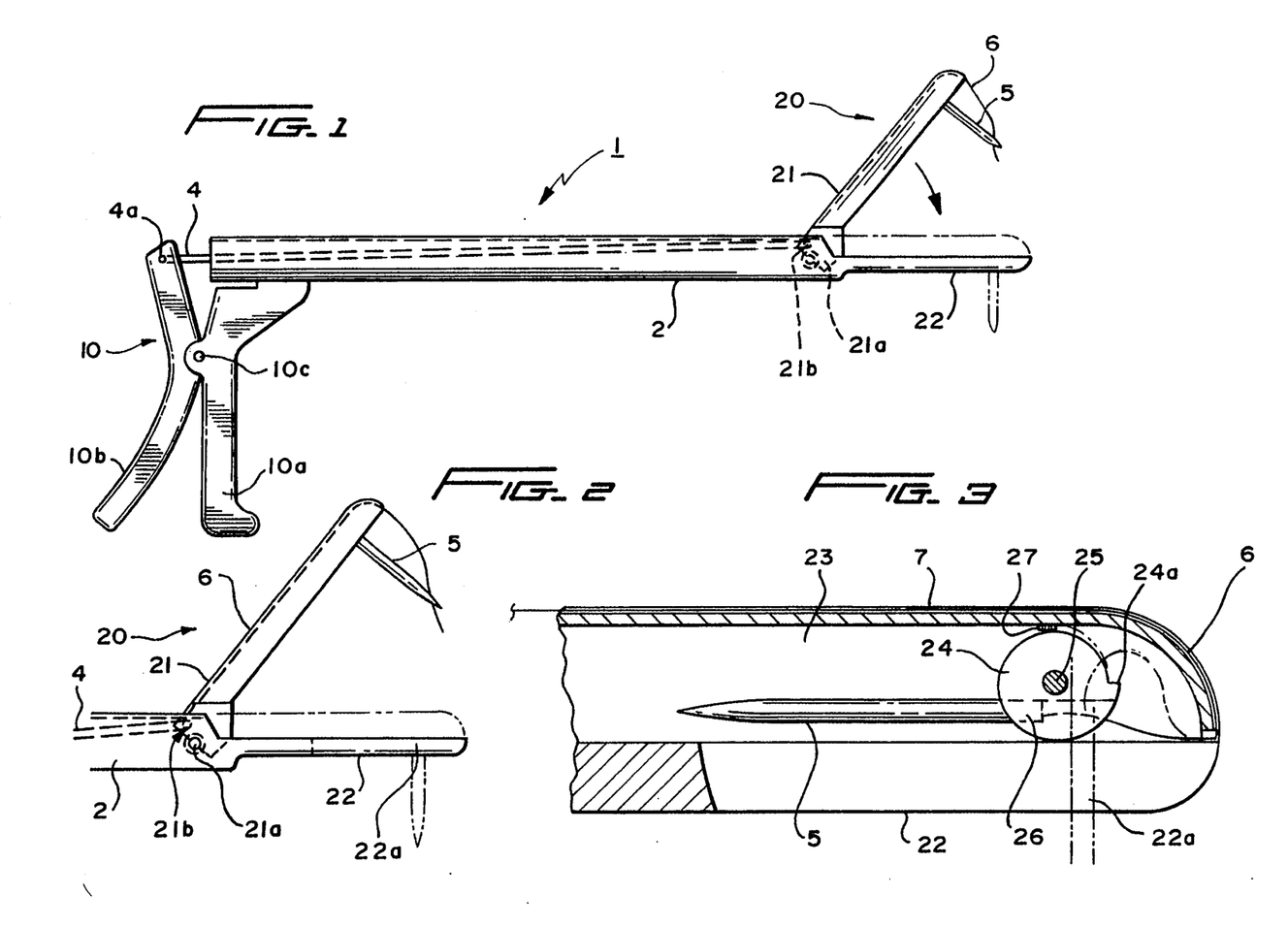
FIG. 1 is an elevational view the suturing device of the present invention.
FIG. 2 is an elevational view illustrating the jaw assembly when the jaws are opened and the needle is deployed from the first jaw member.
FIG. 3 is a detailed elevational view of the jaw assembly and, in a partial cross section, the needle and wheel assembly.

As shown in FIG. 1, the suturing device 1, hereinafter sometimes referred to as the needle holder, comprises an elongated shaft 2 having a handle assembly 10 at one end and a jaw assembly 20 at the distal end thereof, said handle assembly 10 being connected to said shaft 2. Handle assembly 10 comprises a stationary handle 10a and an actuator handle 10b pivotally mounted to stationary handle 10a on a pivot pin 10c. The stationary handle 10a is rigidly attached to said shaft 2 to ensure manipulative control over the entire suturing device assembly. The suturing device 1 further comprises actuating means connecting the handle assembly to the jaw assembly. Preferably, the actuating means is in the form of an actuator rod 4 extending longitudinally within the length of said shaft. The actuator rod 4 is pivotally joined to the actuator handle 10b by pivot means 4a, thereby linking the actuator handle 10a to said jaw element 20. The stationary and actuator handle members and the elongated tube terminating at a distal end into the jaw element are structurally similar to conventional grasping microsurgical instruments commonly associated with non-open surgery. In this manner, the handle assembly 10 provides a grip assembly that may be comfortably held and operated the surgeon.

Although the elongated shaft 2 is shown in FIG. 1 as being substantially cylindrical and having substantially equal diameters at both the proximal and distal ends thereof, it is to be understood that the configuration of the shaft can be fashioned in any form. For instance, the proximal end of the shaft can be tapered such that it terminates in a diameter slightly larger than the diameter of actuator rod 4. Alternatively, the proximal end of shaft 2 can be fitted with a washer, gasket, o-ring or similar element in order to seal the tubular shaft 2 around said actuator rod 4, thereby preventing air from escaping through the shaft.

Figure 1A:
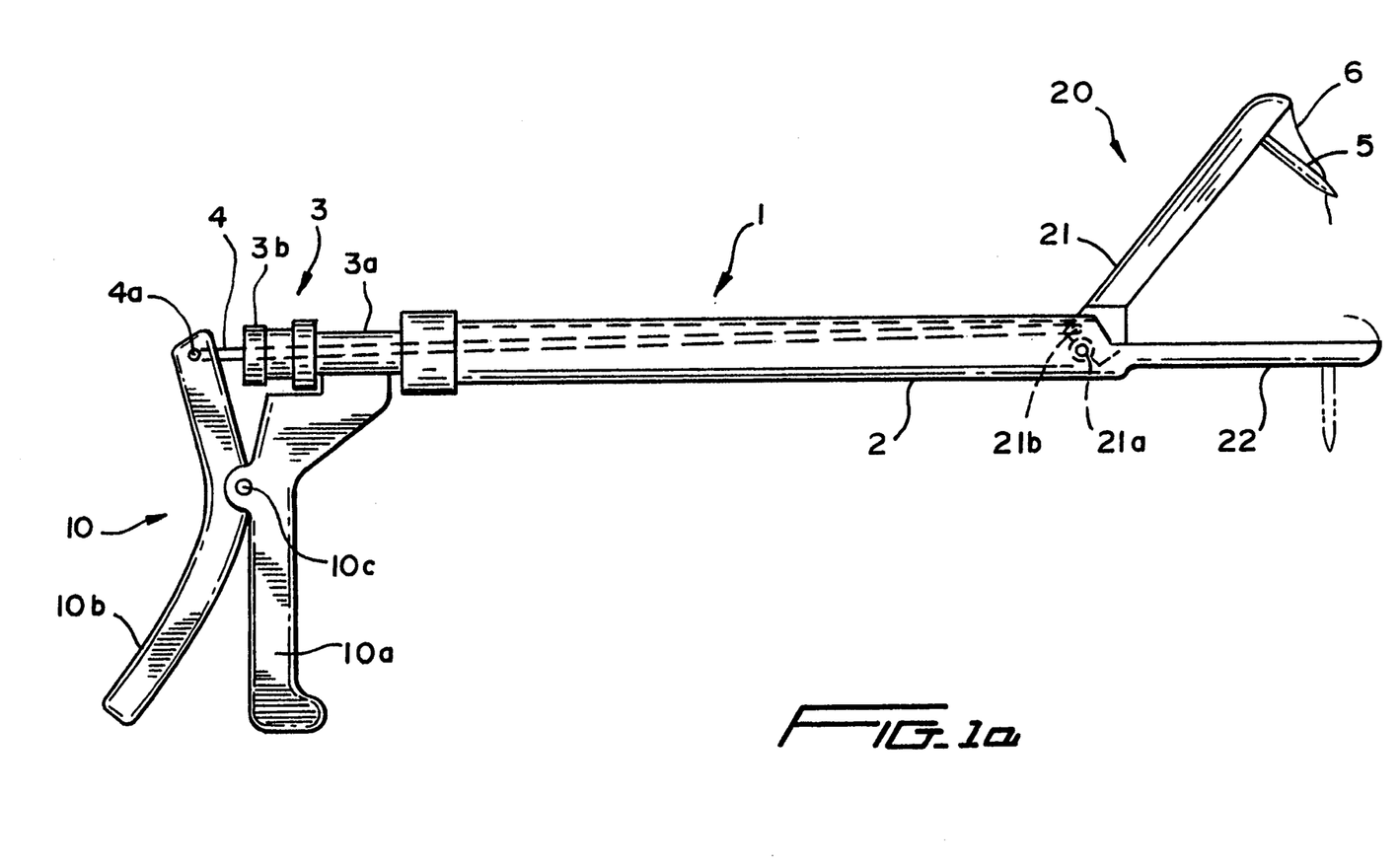
FIG. 1a is an elevational view of an alternate embodiment of the suturing device of the present invention.

In an alternate embodiment shown in FIG. 1a, the suturing device of the present invention further comprises a connecting coupler 3 positioned between and joining the handle assembly 10 and elongated shaft 2. Connecting coupler 3 comprises a tubular shaft 3a having sealing element 3b at the proximal end thereof in order to seal said shaft 3a about said actuator rod 4. The distal end of the connecting coupler 3 may be securely joined to the elongated shaft 2 by any means known in the art. For example, the connecting coupler 3 may be permanently affixed to shaft 2, such as by soldering, welding and the like. Preferably, the connecting coupler 3 is joined to said shaft 2 by means of a fitting for securably mating said coupler to said shaft. Such fittings are well known in the art and include, for example, snap-type fittings, screw-type fittings and the like. In this manner, the elongated shaft 2 can be detached from the connecting coupler in order to facilitate cleaning and sterilizing of the shaft and jaw assembly. Stationary handle 10a of the handle assembly is rigidly affixed to said connecting coupler 3 as shown in FIG. 1a.

As shown in FIGS. 1 and 2, the distal end of the tubular elongated shaft 2 terminates into said jaw assembly 20. Jaw assembly 20 comprises a first or upper jaw member 21 pivotally connected to a second or lower jaw member 22. Preferably, second or lower jaw member 22 is stationary, wherein first or upper jaw member 21 is pivotally connected to said lower jaw member by means of hinge element 21a. Actuator rod 4 is pivotally connected at its distal end to the pivotal upper jaw member 21 at actuator pivot pin 21b. By virtue of this construction, actuator rod 4, when manipulated by actuator handle 10b will impart opening and closing mobility to the pivotal upper jaw member 21.

Figures 4A, 5:
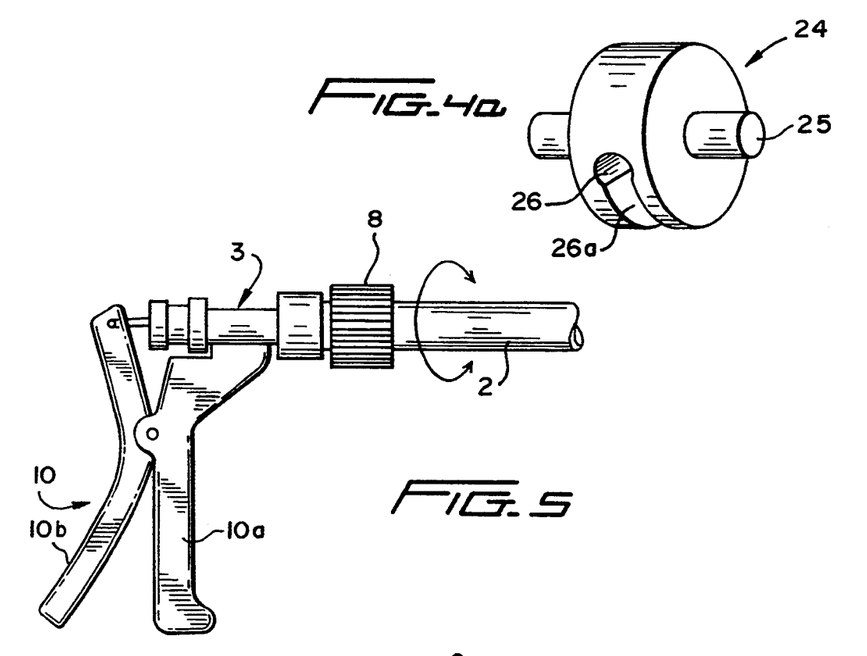
FIG. 4a is a perspective view of the wheel assembly.
FIG. 5 is an elevational view of an alternative embodiment of the suturing device having a rotating collar.
Figure 4B:
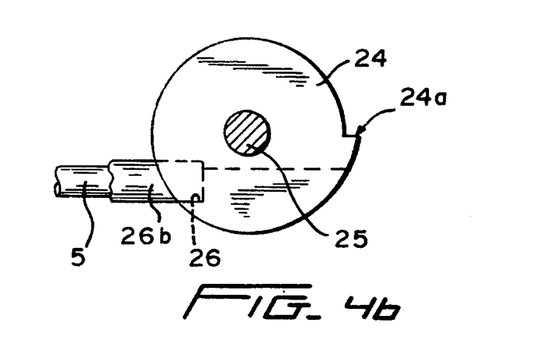
FIG. 4b is an elevational cross section view of the wheel assembly and an alternate embodiment of the needle mount.
Figure 4C:
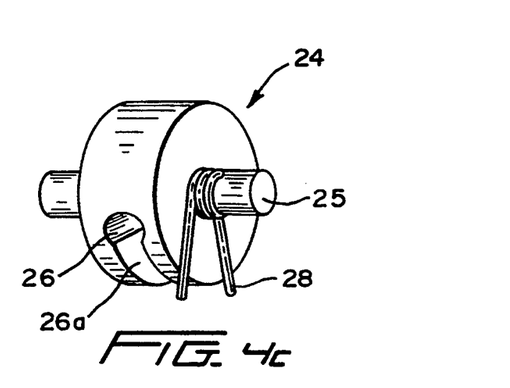
FIG. 4c is a perspective view of an alternate embodiment of the wheel assembly having a spring element.

The first or upper jaw member 21 is provided with a cupped recess or hollow cavity 23 as shown in FIG. 3. Near the distal end of said cavity 23, a wheel assembly 24 is mounted on a pin axle 25. Wheel assembly 24 is rotatably mounted on said pin axle such that the pin axle is parallel to the longitudinal plane of said jaw and said shaft, as shown in FIGS. 3, 4a and 4b. Wheel assembly 24 comprises a shoulder stop 24a, a needle mount 26 and optionally a suture chase 26a which may be in the form of a groove or channel on the circumference of said wheel assembly. Needle mount 26 is provided at a peripheral position on said wheel, in order to hold and secure a surgical needle 5. Needle mount 26 may be fashioned in any manner known in the art capable of holding and securing a surgical needle. For example, the needle mount 26 may be a simple aperture designed to provide a tight and firm fit when the end of surgical needle 5 is inserted therein. In an alternate embodiment, the needle mount 26 may be in the form of an open notch on the wheel periphery designed so that the needle can be clipped and retained therein. In another alternate embodiment, as shown in FIG. 4b, the needle mount 26 further comprises a tube 26b which is positioned and secured within the wheel assembly such that the end of a surgical needle can be inserted and retained therein. The tube may be cut lengthwise in order to enable the suturing thread to be drawn through the suture chase.

The wheel assembly is configured such that when the surgical needle is inserted in needle mount 26, rotation of the wheel in one direction will position the needle lengthwise in a plane parallel to the upper jaw, thereby enabling the needle to lie within said cupped recess. Rotation of said wheel in the opposite direction causes the needle to extend away from the pivotal upper jaw member 21 and outside of the cupped recess. A wheel limit 27, in the form of a node or similar protuberance, is provided on the inner surface of upper jaw member 21 such that it extends into said recess 23 in order to restrict the rotation of wheel assembly 24 upon contact with shoulder stop 24a. Preferably, wheel limit 27 is situated directly above pin axle 25 in order to provide an arc of rotation of about 90°. In this manner, when surgical needle 5 is in a fully protracted position, the needle is perpendicular to pivotal upper jaw element 21. In an alternate embodiment, as shown in FIG. 5c, a spring element 28 may be provided on pin axle 25 and connected to the wheel assembly in order to impose a rotating bias upon said wheel. In this manner, when the jaw members are opened, the spring action causes the wheel to rotate about 90°, thereby biasing the needle 5 in a protracted and deployed position. In this alternate embodiment, wheel limit 27 and shoulder stop 24a can be eliminated.

A suturing thread 6 is affixed to the surgical needle 5 in a manner known in the surgical arts. After the needle has been securably attached to the needle mount 26, the free end of the suturing thread 6 is drawn through the suture chase 26a, alongside the upper exterior surface of pivotal upper jaw element 21 and the exterior surface of the elongated shaft 2 such that the free end is positioned near the handle assembly 10. Preferably, the elongated shaft 2 is provided with a longitudinal groove or channel 7 along the upper surface thereof such that the suturing thread 6 may lie within said longitudinal groove.

The needle holder of the present invention can be used with a variety of surgical needles, including straight and various curvature needles of different sizes. Stationary lower jaw 22 is provided with a needle notch 22a as shown in FIG. 2, which may be in the form of an aperture, slot or similar opening within the distal end of said lower jaw. Said notch 22a enables upper jaw member 21 to close upon the lower jaw member 22 when the needle 5 is deployed. In this manner, as shown in FIG. 2, any conventional surgical needle can be inserted in the needle mount 26 and can easily pass through the needle notch 22a, thereby allowing the upper and lower jaw members to be closed upon each other while the needle is protracted from the upper jaw member.

Figures 7, 8, 9, 10:
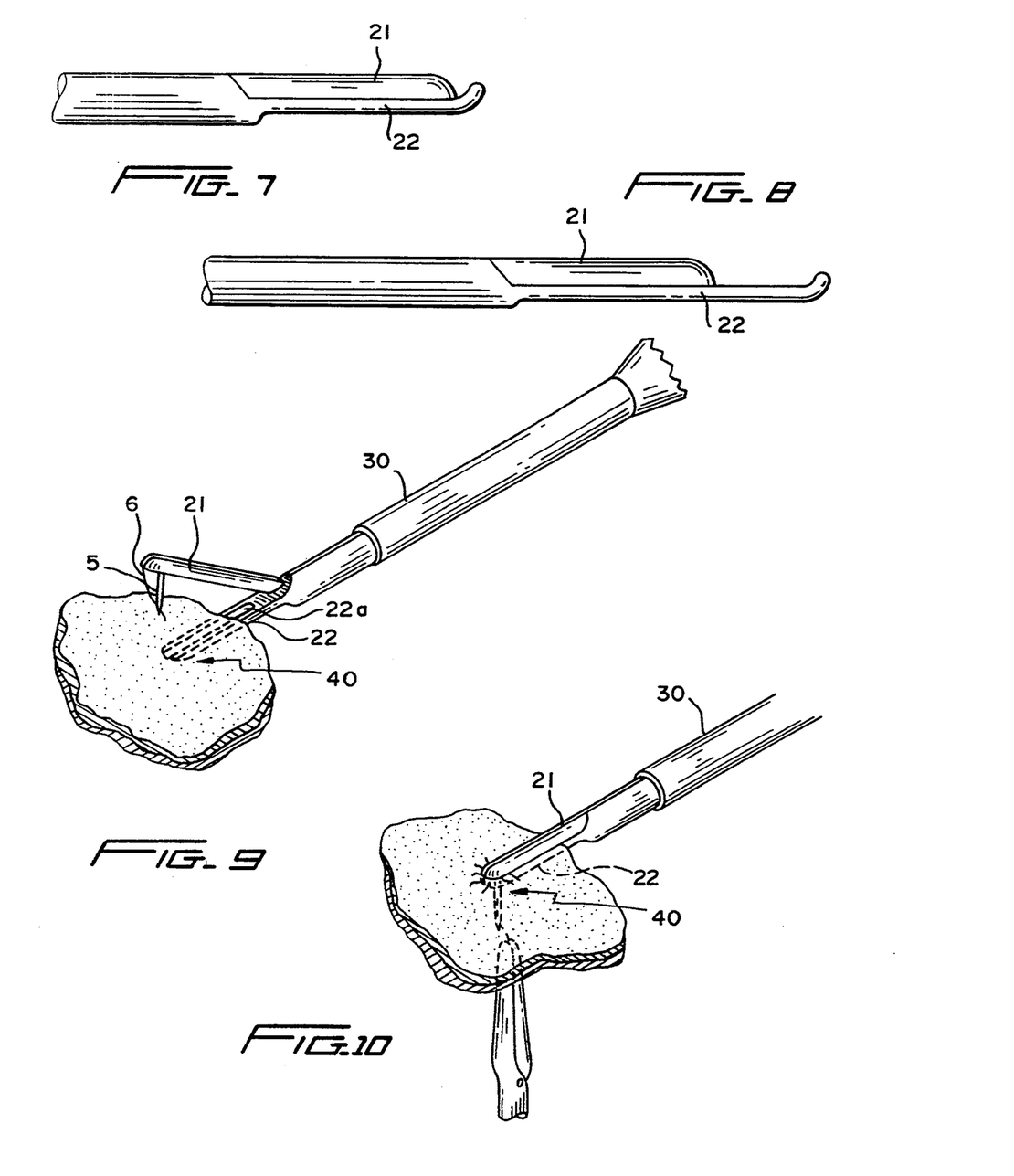
FIG. 7 shows an alternate embodiment of the jaw assembly.
FIG. 8 shows an alternate embodiment of the jaw assembly.
FIG. 9 illustrates operation of the suturing device.
FIG. 10 illustrates operation of the suturing device.

First and second jaw members 21 and 22 may be fashioned in any manner to provide suitable clamping means as illustrated in FIGS. 2, 7 and 8. Either of both of said jaw members may be straight, bent at an angle or hooked. Preferably, the upper jaw member is straight and the lower jaw member is either straight or bent upward as shown in FIGS. 7 and 8. Additionally, the gripping surfaces of either or both of said jaw members may be smooth or may be knurled to enhance grasping and stabilizing the tissue. Preferably, the first and second jaw members have knurled gripping surfaces.

In another alternate embodiment, the suturing device of the present invention may be further adapted to provide a means to control and facilitate radial rotation of the jaw element 20. As shown in FIG. 5, a rotating collar 8 is installed on the elongated shaft 2 and rotatably joined to connecting coupler 3 by means well known in the art. The rotating collar 8 preferably comprises a knurled collar or other suitable means which both joins the proximal end of said shaft to the handle assembly and also radially rotates the shaft with respect to said handle assembly 10. Thus, while holding the handles 10a and 10b with one hand, the surgeon can rotate the shaft with the other hand by gripping and rotating said collar in a clockwise or counter-clockwise direction. By twisting the rotating collar and shaft, the jaw element 20 is rotated at the distal end of the shaft.

Figure 6:
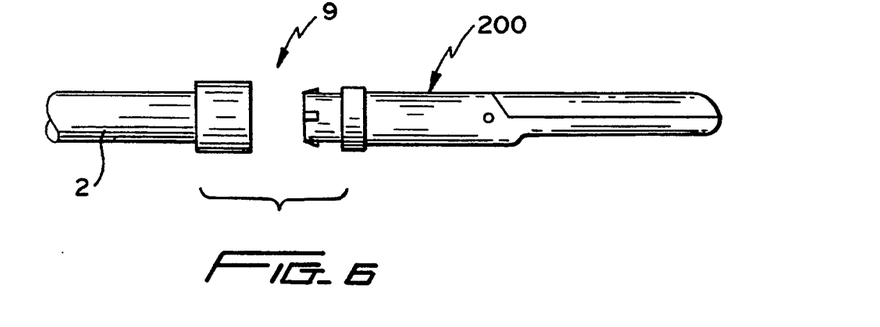
FIG. 6 shows an alternative embodiment of the suturing device having the jaw assembly in the form of a disposable head.

The laparoscopic needle holder of the present invention can be either a multiple use instrument, as described hereinabove, or in an alternative embodiment, can be a disposable, single use instrument. As shown in FIG. 6, the suturing device is provided with a joint member 9 located at the distal end of the shaft. Joint member 9 connects the elongated shaft 2 to a disposable jaw element 200, sometimes hereinafter referred to as a disposable head. The joint member comprises a fitting for securably mating the disposable head with the shaft 2. Such fittings are well known in the art and include snap-type fittings, screw-type fittings and the like. Preferably joint member 9 is fashioned to provide a snap-on fitting, wherein the disposable jaw element 200 is pushed axially into the fitting. In this manner, after completion of the suturing operation, the disposable head may by pulled off the shaft and discarded.

The use and operation of the suturing device will be described, partially with reference to FIGS. 9 and 10. Actuator handle 10b is squeezed against stationary handle 10a such that the resulting manipulation of actuator rod 4 causes pivotal upper jaw 21 to open away from stationary lower jaw 22. A suturing thread 6 is affixed to surgical needle 5 and needle 5 is inserted into needle mount 26 of wheel assembly 24. The wheel assembly is rotated manually such that the needle lies within the cupped recess 23 and further manipulation of the actuator handle causes upper jaw 21 to close upon stationary jaw 22. The suturing thread 6 is drawn away from the needle and arranged in groove 7 such that the free end is located near the handle assembly 10. The suturing device 1, now in the closed position, is introduced into a trocar or similar conduit 30 and guided to the operative site 40 of tissue to be sutured. A clamping device 50 is inserted into a second trocar (not shown) and guided to the operative site near the suturing device of the present invention.

To initiate the suturing operation, the actuator handle 10b is manipulated thereby causing the upper jaw 21 to open away from lower jaw 22. The proximal free end of the suturing thread 6 is pulled taut thereby effecting the surgical needle 5 in needle mount 26 to be rotated about wheel assembly 24 such that the needle is in a fully protracted position, as shown in FIG. 9. The tissue 40 to be sutured is positioned between opposed jaw members 21 and 22 and upper jaw member 21 is closed upon lower jaw 22, thereby forcing needle 5 through the tissue 40 and through needle notch 22a, as shown in FIG. 10. In this manner, the sutured tissue remains gripped between the jaws of the device after being pierced by the needle, and remains under the control of the surgeon, thereby facilitating further tissue manipulations. The clamping member 50 thereafter grasps the needle 5, thereby releasing the needle from the needle mount 26 and the needle and suturing thread are pulled through the tissue. The needle holder 1 and clamping device 50 are withdrawn from the trocar, an extracorporeal knot is tied and pushed down the trocar to the sutured site.

Alternatively, after the needle has been detached from the needle mount and pulled through the tissue, the needle, held by clamping device 50 may be reinserted into needle mount 26 of needle holder 1. The needle holder then may be guided to next site to be sutured and a second tissue-piercing procedure can be performed, identical to the first operation.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A suturing device comprising an elongated shaft having a handle assembly at the proximal end, a jaw assembly at the distal end thereof comprising first and second jaw members pivotally connected, and actuator means connected to said handle assembly and to one of said first jaw member and second jaw member for pivoting said first jaw member relative to said second jaw member; wherein the first jaw member comprises a recess having means for securably retaining a needle therein and for deploying the needle to a protracted position from the first jaw member, wherein said means for retaining and deploying the needle comprises a wheel assembly configured in such a manner that rotation of the wheel assembly in one direction allows the needle to lie within the cupped recess and rotation of the wheel assembly in the opposite direction deploys the needle to a protracted position.

2. A suturing device in accordance with claim 1, wherein said actuator means comprises an actuator rod extending longitudinally within the length of said shaft, said actuator rod being connected at its proximal end to said handle assembly and connected at its distal end to said jaw assembly.

3. The suturing device in accordance with claim 1, wherein said wheel assembly is rotatably mounted on a pin axle such that the pin axle is parallel to the longitudinal plane of said first jaw member, said wheel assembly further comprises a needle mount for securably retaining a surgical needle.

4. The suturing device in accordance with claim 3, wherein said first jaw member further comprises a wheel limit for restricting the rotation of the wheel assembly.

5. The suturing device according to claim 4, wherein said wheel assembly further comprises a shoulder stop such that rotation of said wheel assembly is restricted when said shoulder stop contacts said wheel limit.

6. The suturing device according to claim 1, wherein a needle notch is provided in said second jaw member to allow passage of a surgical needle therethrough.

7. The suturing device according to claim 1, wherein said shaft is joined to said handle assembly by means of a connecting coupler.

8. The suturing device according to claim 7, wherein said shaft further comprises means for radial rotation of the jaw assembly.

9. A suturing device according to claim 1, wherein said jaw assembly is mounted in a disposable head, said disposable head being connected to said tubular elongated shaft by means of joint fitting.

10. The suturing device in accordance with claim 1, wherein manipulation of said handle assembly causes said first and second jaw members to positively grasp and stabilize tissue which is to be sutured.

11. A suturing device comprising a tubular elongated shaft having a handle assembly at the proximal end and a jaw assembly at the distal end thereof, said elongated tubular shaft terminating into a stationary lower jaw member which is hingedly connected to a pivotal upper jaw member; said elongated tubular shaft further comprising an actuator rod extending longitudinally within the length of said shaft, said actuator rod being connected at its proximal end to said handle assembly and connected at its distal end to said upper jaw member; wherein the underside of said upper jaw member is provided with a cupped recess having means for retaining a needle therein and for deploying the needle to a protracted position, wherein said means for retaining and deploying the needle comprises a wheel assembly configured in such a manner that rotation of the wheel assembly in one direction allows the needle to lie within the cupped recess and rotation of the wheel assembly in the opposite direction deploys the needle to a protracted position.

12. The suturing device in accordance with claim 11, wherein said upper jaw member further comprises a wheel limit for restricting rotation of said wheel assembly; and wherein the wheel assembly further comprises a needle mount for securably retaining a needle and a shoulder stop, such that rotation of the wheel is restricted when said shoulder stop contacts said wheel limit.

13. The suturing device in accordance with claim 11, wherein said shaft is joined to said handle assembly by means of a connecting coupler.

14. The suturing device in accordance with claim 13, wherein said shaft further comprises means for radial rotation of the jaw assembly.

* * * * *